United States Patent [19]

Hosohara et al.

[11] Patent Number: 5,365,169

[45] Date of Patent: Nov. 15, 1994

[54] REMOTE FIELD EDDY CURRENT FLAW DETECTOR FOR METAL MATERIAL INCLUDING ATTENUATOR, ADDER, PHASE SHIFTERY AND PHASE COMPARATOR

[75] Inventors: Yasuharu Hosohara; Kiwamu Suzuki, both of Yokohama; Shigeru Fujiwara; Toshihide Kawabe, both of Kure, all of Japan

[73] Assignees: Tokyo Gas Co., Ltd., Tokyo; CXR Co., Ltd., Hiroshima, both of Japan

[21] Appl. No.: 14,875

[22] Filed: Jan. 28, 1993

Related U.S. Application Data

[62] Division of Ser. No. 740,388, Aug. 5, 1991, Pat. No. 5,210,492.

[30] Foreign Application Priority Data

Apr. 22, 1991 [JP] Japan .................................. 3-90685
May 27, 1991 [JP] Japan ................................ 3-121291

[51] Int. Cl.$^5$ ............................................ G01N 27/90
[52] U.S. Cl. .................................... 324/233; 324/220; 324/241; 324/242
[58] Field of Search ................................ 324/219–221, 324/233, 238–243

[56] References Cited

U.S. PATENT DOCUMENTS

| | | | |
|---|---|---|---|
| 3,676,772 | 7/1972 | Lee | 324/233 |
| 4,191,922 | 3/1980 | Harris et al. | 324/233 X |
| 4,207,520 | 6/1980 | Flora et al. | 324/233 X |
| 4,368,429 | 1/1983 | Jamison | 324/233 X |
| 4,520,317 | 5/1985 | Peterman | 324/326 |
| 4,652,823 | 3/1987 | Sutton | 324/240 |
| 4,849,693 | 7/1989 | Prince et al. | 324/233 X |

FOREIGN PATENT DOCUMENTS

| | | |
|---|---|---|
| 1329302 | 9/1973 | United Kingdom . |
| 1403734 | 8/1975 | United Kingdom ................ 324/240 |

*Primary Examiner*—Gerard R. Strecker
*Attorney, Agent, or Firm*—Nixon & Vanderhye

[57] ABSTRACT

The present invention relates to a flaw detector for metal material for maintaining and managing pipelines using a remote field eddy current sensor. An AC signal having a constant level and shifted by predetermined phase angle is added to signals received in receiving coils of the remote field eddy current sensor to obtain accurate phase detection in a normal, nonflawed portion of the pipeline to be tested (e.g. uniform thickness, no holes, etc.). By preventing generation of abnormal flaw data, precise diagnosis of the pipeline can be performed. An AGC circuit may be used to maintain at a constant level of received signal. Two sets of spaced apart receiving coils are spaced from an exciting coil a distance greater than a predetermined distance (about two time the pipeline diameter). The set of receiving coils closest to the exciting coil has a greater number of coil turns than the other set. This coil configuration generates sensed coil differential signals having sufficient signal amplitude to permit stabilized and accurate phase detection and comparison for nonflawed and gradually flawed regions in the pipe.

2 Claims, 5 Drawing Sheets

FIG. 6
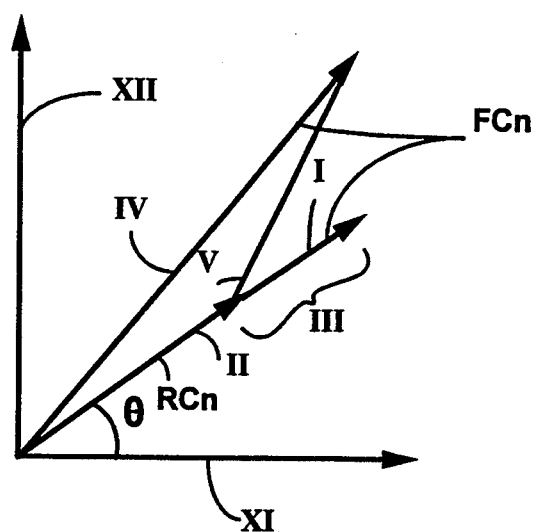
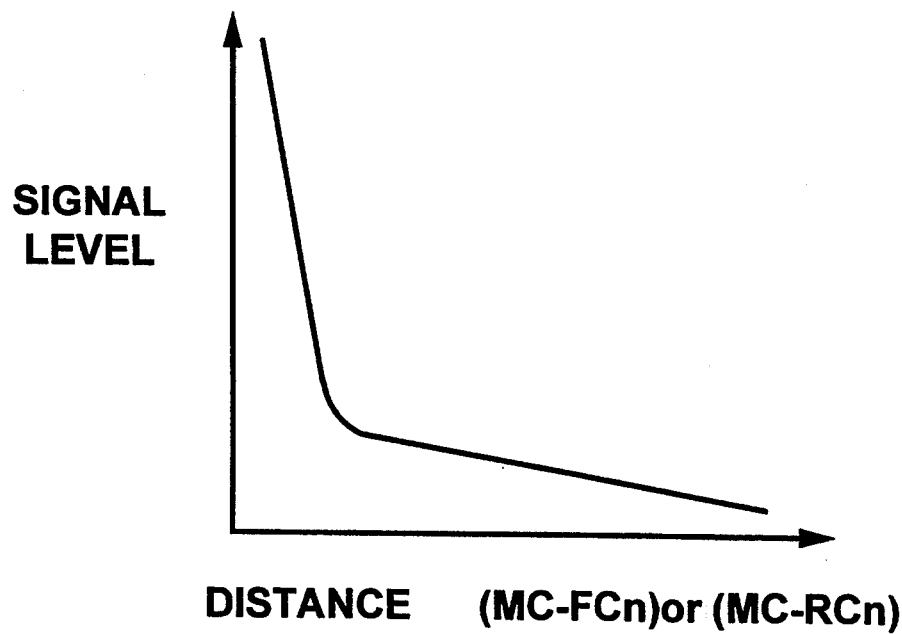
FIG. 7

REMOTE FIELD EDDY CURRENT FLAW DETECTOR FOR METAL MATERIAL INCLUDING ATTENUATOR, ADDER, PHASE SHIFTERY AND PHASE COMPARATOR

This is a division of application Ser. No. 07/740,388, filed Aug. 5, 1991, now U.S. Pat. No. 5,210,492.

FIELD OF THE INVENTION

The present invention relates to a flaw detector for metal material which can maintain and manage pipelines such as a buried gas pipeline, a chemical plant pipeline and a heat exchanger pipeline using the remote field eddy current method, to a remote field eddy current sensor which is suitable for such flaw detector.

BACKGROUND OF THE INVENTION

When detecting flaws of metal materials such as pipelines by using the remote field eddy current method, a remote field eddy current sensor connected to a cable for transmitting signals is inserted into the pipeline, and exciting voltage is supplied to the sensor. The sensor includes an exciting coil and one or more receiving coils spaced from the exciting coil in the longitudinal direction of the pipeline at a predetermined distance being two times longer than a diameter of the pipeline. A relatively low frequency voltage having a frequency such as from tens Hz to hundreds Hz and a voltage from several V to tens V is used as the exciting voltage signal.

Electromagnetic waves generated by the exciting signal are separated into two groups; one passes through a thickness of the pipeline to be tested and the other propagates in the pipeline. The latter is rapidly attenuated and hardly transmitted, since, if the pipeline is considered to be a wave guide, its frequency is much lower than the cut-off frequency. The former wave is called an indirect transmitting wave and transmits along the exterior of the pipeline and is gradually attenuated. At the same time, a part of the former wave passes again through the thickness of the pipeline, permeates into the pipeline and is received by the receiving coil.

The received signal detected by the receiving coil has very small magnitude (from several micro V to tens micro V), since it passes through the pipeline twice. In addition, the phase thereof is changed by the skin effect in passing through the thickness of the pipeline. In the remote field eddy current method, that phase change has good linearity relative to the thickness of the pipeline and therefore may be used as an indication of pipe thickness and the presence of flawed pipe walls (i.e. areas of nonuniform thickness).

In the remote field eddy current method, when the eddy current sensor including the exciting coil and the receiving coil is inserted into the pipeline to be tested and progressed at a constant velocity, the amplitude of the received signal is changed and phase detected flaw data is mixed with phase detection noise, since the dielectric constant of the pipeline to be tested is not uniform and the eddy current sensor vibrates as a result of the progressing movement. Thus, the detected flaw data may be converted abnormally. Further, when another type of the eddy current sensor is used and wherein a plurality of the receiving coil is arranged annularly in the inner wall of the pipeline, it is difficult to make accurate diagnosis of the pipeline, since abnormal flaw data is accumulated.

The remote field eddy current method can be classified into two types; an absolute type in which a plurality of receiving coils are arranged concentrically at the rear of an exciting coil and a differential type which includes a front group of the receiving coils concentrically arranged and a rear group of the receiving coils arranged at the rear of the front group. In the absolute type, the number of turns of each coil of the group of the receiving coils is the same, respectively, and a plurality of receiving coils is connected with a measuring device by a required number of pair cables for producing a sensor signal. On the other hand, in the differential type, the number of turns of the front group receiving coils and the rear group receiving coils is the same, respectively, and the front coil and the rear coil are differentially connected to each other and are connected with a measuring device by a required number of pair cables.

While in the absolute type sensor the received signal can be always received in a part of the pipeline without flaws, in the differential type sensor, the received signal is usually received with a very small magnitude except in a part of the pipe having a changed shape such as a local flaw, because of the differential connection. This phenomenon also is found when using another type of receiving coil (normal direction coil) in which magnetic path by the remote field eddy current is arranged normal to the axis of the exciting coil.

When using the group of receiving coils including the differential type coil or the normal direction coil in the remote field eddy current method in a normal part of material to be tested, it is difficult to get sufficient received signal in order to obtain a stable measurement of phase. In addition, phase detected flaw data is often mixed with noise, and the flaw data may be converted erroneously.

Further, when using the remote field eddy current sensor in which a plurality of the receiving coils are arranged annularly in the inner wall of the pipeline, it is difficult to make accurate diagnosis of the pipeline because of the accumulation of erroneous flaw data.

In the differential type sensor, the number of turns of each receiving coil of the front group and the rear group of the receiving coils is the same, respectively, and required number of coils is parallel or serially connected in the front group or the rear group. The front coils and the rear coils are differentially connected to each other and connected with the measuring device by the required number of pair cables.

In the absolute type of the remote field eddy current sensor having the above mentioned construction, while stable diagnosis can be made because relatively high level sensor signal can be provided and the sensor is suitable for the detection of gradually progressing flaws in part FW of the pipeline to be tested, the detecting sensitivity to a locally flawed part of the pipeline FS is low and frequently the sensor cannot detect such small local flaws. On the other hand, in the differential type of the remote field eddy current sensor, while the flawed part of the pipe can be detected by the signal level difference between the front group of the receiving coils and the rear group of the receiving coils, the differential sensor can detect local flaws because of its high sensitivity. However, it is hard to measure the difference generated for gradually progressing flaws. As a result, it is hard to make stable phase detection because the differential signal is too small.

In both types of remote field eddy current sensors, since sensor measurement is performed not only by strength and weakness of the sensor signal level, but also by computing width or depth of the flaw by phase delay characteristics of an acquired sensor signal, it is important to get stability of the phase detection.

SUMMARY OF THE INVENTION

The first object of the present invention is to remove influences of noise in phase detection.

The second object of the present invention is to provide a flaw detector for metal material which can decrease phase detecting noise by stabilizing received signal levels by automatically adjusting received signals produced by the receiving coil to a predetermined level and which can improve the S/N ratio of flaw data by such decrease of phase detecting noise.

The third object of the present invention is to provide a flaw detector for metal material which can prevent the accumulation of the abnormal flaw data caused by phase detecting noise generated when using a remote field eddy current sensor with a plurality of receiving coils.

The fourth object of the present invention is to provide a flaw detector for metal material which prevents generation of abnormal flaw data by overlaying the received signal produced by the receiving coil with AC signals having a predetermined phase and amplitude.

The fifth object of the present invention is to provide a flaw detector for metal material which can prevent accumulation of abnormal flaw data by phase detecting noise included in the flaw data when using the remote field eddy current sensor including a plurality of receiving coils arranged annularly in the inner wall of a pipeline.

The sixth object of the present invention is to provide a remote field eddy current sensor which is suitable for a flaw detector for metal material that can produce sensor signals by which stable phase data for both gradually progressing flaws and local flaws can be obtained by employing a construction in which the number of turns of the front receiving coils is greater than that of the rear receiving coils.

A flaw detector for metal material according to the present invention comprises a reference signal generator means for generating a reference signal; an exciting coil for receiving an exciting signal having the same phase as that of said reference signal to generate remote field eddy currents in metal material to be tested; a receiving coil, spaced from said exciting coil at a predetermined distance, for receiving said remote field eddy currents to generate a received signal; an automatic amplitude adjustor means for adjusting the received signal provided from said receiving coil to a constant level; and a flaw data generator means for comparing said received signal adjusted by said automatic amplitude adjusting means with said reference signal to generate flaw data.

Further, the flaw detector for metal material according to the present invention may comprise a plurality of said receiving coils, said automatic amplitude adjusting means and said detected flaw data generating means.

The exciting signal provided by the reference signal generator means is transmitted to the exciting coil. The received signal produced by the receiving coil is transmitted to the received signal processing module in a received signal circuit. A compare signal produced by a compare signal generator means in the exciting signal producing means and transmitted to a received signal processing module is phase-compared by a phase comparator, and the amplitude level of the received signal is automatically adjusted in AGC circuit. Thus, phase detecting noise included in the flaw data produced by the phase comparator is decreased and the S/N ratio of the flaw data can be improved.

Further, a flaw detector for metal material according to the present invention comprises a reference signal generator means for generating reference signal; an exciting coil for receiving exciting signal having the same phase as that of said reference signal to generate remote field eddy currents in metal material to be tested; a receiving coil, spaced from said exciting coil at a predetermined distance, for receiving said remote field eddy currents to generate a received signal; an AC signal generator means for generating constant level AC signal by phase-shifting said reference signal at a predetermined phase angle; a signal adder means for adding said AC signal provided by said AC signal generating means to said received signal; a detected flaw data generating means for comparing said AC signal added by said adder means and said received signal with said reference signal to generate flaw data.

Further, the flaw detector for metal material according to the present invention may comprises a plurality of said receiving coils, said automatic amplitude adjusting means and said flaw data generating means.

When an exciting signal is applied to the exciting coil of the remote field eddy current sensor, a received signal is generated in the receiving coils. After in-phase noise of the received signal is removed using a differential amplifier of received signal interference and a high frequency component thereof is removed by a low pass filter, the received signal is supplied to the other input of the adder. On the other hand, the exciting signal supplied to the adding terminal of the added signal processing module is attenuated to a level determined by an amplitude setting means of the attenuator of an added signal generating module. Then, if a phase angle is predetermined by a phase angle setting device in the phase shifter to, for example 15 degrees, the added signal having 15 degrees of phase angle delay is supplied to the one input of the received signal processing module.

Further, a remote field eddy current sensor according to the present invention comprises an exciting coil for generating remote field eddy current to metal material to be tested; a first receiving coil, spaced from said exciting coil at a predetermined distance, for receiving said remote field eddy current; a second receiving coil, spaced from said exciting coil at further distance than said predetermined distance, for receiving said remote field eddy current, where the number of turns of the second receiving coil is fewer than that of said first receiving coil. Therefore, stable phase data for both of the gradually progressing flaw and local flaw can be obtained.

DESCRIPTION OF THE DRAWINGS

FIG. 6 is a signal vector changing diagram of local flaw associated with FIG. 1.

FIG. 7 is a characteristics diagram illustrating signal level to a distance between an exciting coil and a receiving coil.

DETAILED DESCRIPTION OF THE PREFERRED EMBODIMENT

Hereinafter, one exemplary embodiment of a flaw detector for metal material according to the present invention will be illustrated with reference to FIG. 1.

Figure 1:
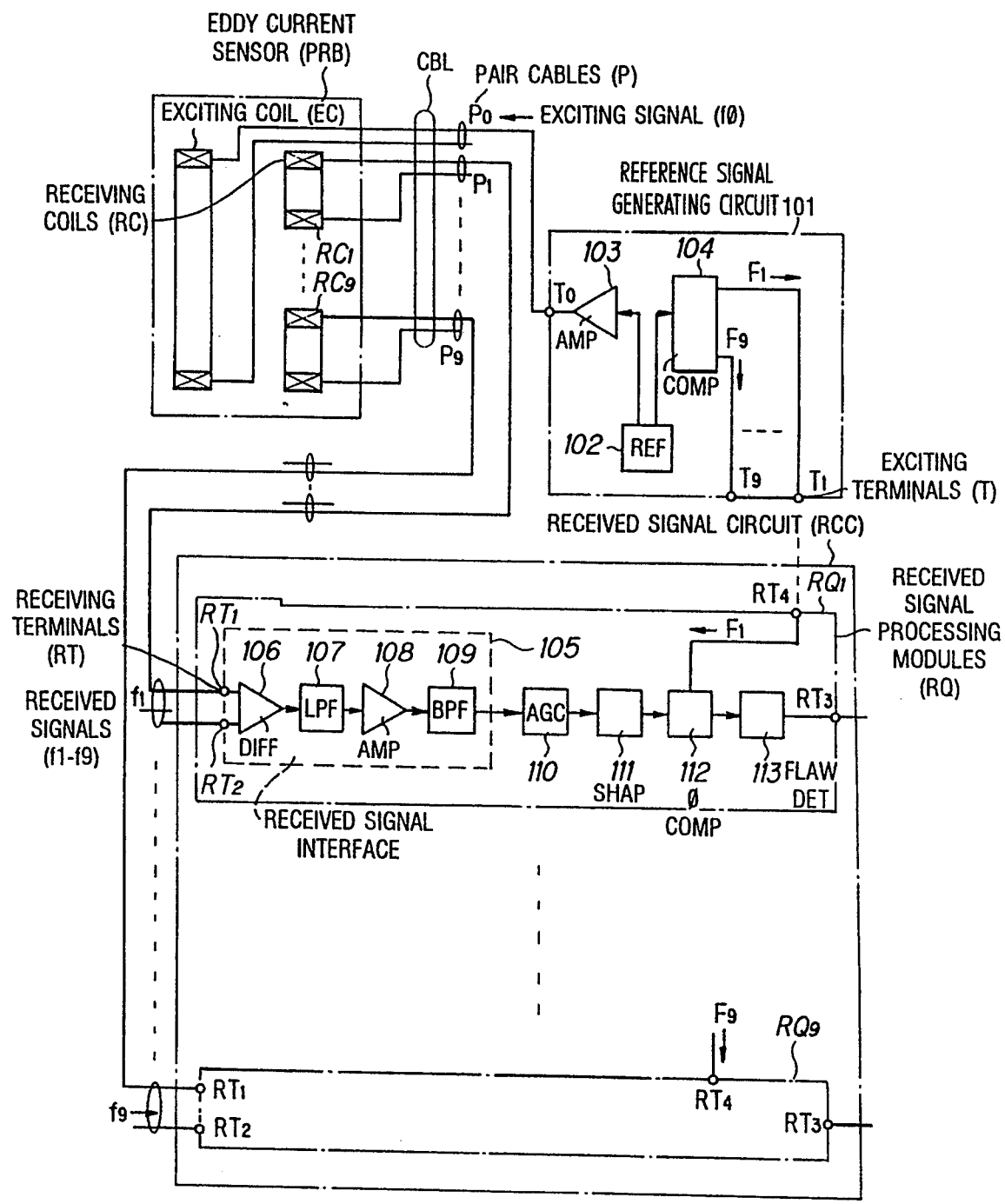
FIG. 1 is a block diagram of one embodiment of a flaw detector for metal material according to the present invention.

As shown in FIG. 1, a flaw detector or metal material according to the present invention comprises an eddy current sensor PRB including an exciting coil EC and a plurality of receiving coils RCn (for the purpose of description, n is referred to as 1 to 9), an exciting signal generating circuit 101 including a reference signal generator 102, an exciting signal output amplifier 103 and a compare signal generating circuit 104 and a received signal circuit RCC including a plurality of the received signal processing modules $RQ_1$ to $RQ_9$. An exciting side terminal $T_0$ of the exciting signal producing circuit 101, receiving side terminals $RT_1$ and $RT_2$ . . . of the received signal processing modules $RQ_1$ to $RQ_9$ of the received signal circuit RCC are connected to pair cables $P_0$ to $P_9$ of cables CBL. Exciting signal $f_0$ produced by the pair cables $P_0$ is received in the exciting coil EC and received signal $f_1$ to $f_9$ is transmitted by the pair cables $P_1$ to $P_9$. If employing a special cable CBL wherein exciting signal having higher voltage than that of received signal $f_1$ to $f_9$, compare signal $F_2$ to $F_9$ may have same phase as the exciting signal $f_0$.

Each receiving terminal $RT_1$ to $RT_2$ of the received signal processing modules $RQ_1$ to $RQ_9$ of the received signal circuit RCC is connected to an input side of a differential amplifier of a received signal interface 105. An output side of the differential amplifier 106 is connected to an input side of an AGC circuit 110 through a low pass filter 107, a receiving amplifier 108 and a band pass filter 109. Homopolar noise generated in the pair cables $P_1$ to $P_9$ is removed by the differential amplifier. High frequency components of the received signal $f_1$ to $f_9$ generated by the differential amplifier 106 are removed by the low pass filter 107. The received signal $f_1$ to $f_9$ whose high frequency components are removed by the low pass filter 107, is supplied to input side of the AGC circuit 110 through the band pass filter 109. After being converted to a predetermined level of amplitude by the AGC circuit 110, the received signal is supplied to a waveform shaper 111. Output side of the waveform shaper 111 is connected to one input side of a phase comparator 112. The output side of the phase comparator 112 is connected to a receiving terminal $RT_3$ through a flaw detecting signal generating device 113.

Each receiving terminal $RT_4$ . . . of the received signal processing modules $RQ_1$ to $RQ_9$ is connected to exciting terminals $T_1$ to $T_9$ of the exciting signal generating circuit 101. Each phase comparator 112 of the received signal modules $RQ_1$ to $RQ_9$ compares processed received signal $f_1$ to $f_9$ supplied into one input side thereof with the compare signals $F_1$ to $F_9$ supplied into another input side thereof.

In the embodiment of the flaw detector having the above construction, since the amplitude level of the received signals $f_1$ to $f_9$ from the band pass filter 109 are automatically adjusted to the predetermined level by the AGC circuit 110, even the magnetic permeability of a pipeline to be tested is not uniform, and therefore the level of the received signal supplied to the phase comparator 112 does not change. Thus, phase detection noise mixed into the flaw data generated from the phase comparator 112 decreases and S/N ratio of the flaw detecting data improves by such decrease of the phase detection noise. If a plurality of receiving coils, the automatic amplitude adjusting means and the flaw data generator is provided, accumulation of abnormal flaw data caused by the phase detection noise included in the flaw data can be prevented.

Figure 2:
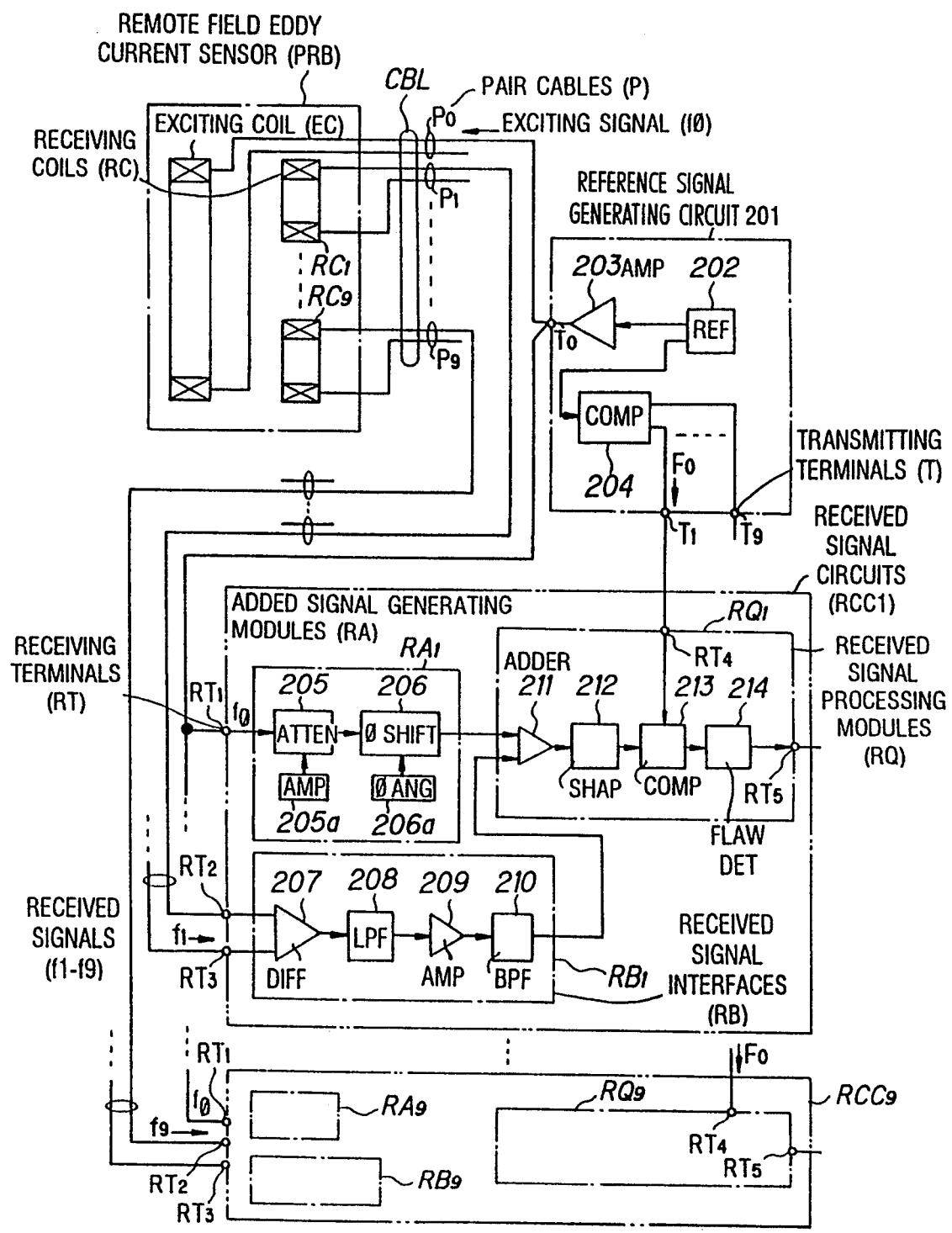
FIG. 2 is a block diagram of another embodiment of a flaw detector for metal material according to the present invention.

FIG. 2 is a block diagram of another embodiment of a flaw detector for metal material according to the present invention.

In the FIG. 2, a flaw detector comprises a remote field eddy current sensor PRB including an exciting coil EC and a plurality of the receiving coils FCn (for convenience to illustrate, n is referred to as 1 to 9 and a differential coil may be used), an exciting signal generating circuit 201 including a reference signal generator 202, an exciting signal generating amplifier 203, a compare signal generating circuit 204, and received signal circuits $RCC_1$ to $RCC_9$ including received signal processing modules $RQ_1$ to $RQ_9$, added signal generating modules $RFA_1$ to $RA_9$ and received signal interfaces $RB_1$ to $RB_9$.

Output side of the reference signal generator 202 of the exciting signal generating circuit 201 is connected to the input side of the exciting signal amplifier 203 and output side of the exciting signal generating amplifier 203 is connected to a terminal $T_0$, respectively. The transmitting terminal $T_0$ is connected to the exciting coil EC of the remote field eddy current sensor PRB through a pair cable $P_0$ of the cable CBL. Each receiving coil $RC_1$ to $RC_9$ is connected to receiving terminals $RT_2$ and $RT_3$ of the received signal circuits $RC_1$ to $RC_9$ through pair cables $P_1$ to $P_9$ of the cable CBL. Said pair cable $P_0$ receives the exciting signal $f_0$ and the pair cables $P_1$ to $P_9$ transmit the signals $f_1$ to $f_9$. The transmitting terminal $T_1$ is connected to an adding terminal $RT_1$ of the received signal circuits $RCC_1$ to $RCC_9$.

Output side of the reference signal generator 202 of the exciting signal generating circuit 201 is connected to input side of the compare signal generating circuit 204 and nine output sides of the reference signal generating circuit 204 are connected to the reference signal terminals $T_1$ to $T_9$. The reference signal terminals $T_1$ to $T_9$ are connected to a compare terminal $RT_4$ of the received signal circuits $RCC_1$ to $RCC_9$.

The added signal generating modules $RA_1$ to $RA_9$ include an attenuator 205, an amplitude setting device 205a, a phase shifter 206 and a phase angle setting device 206a. Input side of the attenuator 205 is connected to the adding terminal $RT_1$ and output side thereof is connected to input side of the phase shifter 206. Output side of the phase shifter 206 is connected to one input side of an adder 211, described latter, of the received signal processing modules $RQ_1$ to $RQ_9$.

Received signal interfaces $RB_1$ to $RB_9$ are connected to a differential amplifier 207, a low pass filter 208, a receiving amplifier 209 and a band pass filter 210, respectively. Output side of the differential amplifier 207 is connected to another input side of said adder 211 through the low pass filter 208, the receiving amplifier 209 and the band pass filter 210.

The receive signal processing modules $RQ_1$ to $RQ_9$ comprise the adder 211, a waveform shaping circuit 212, a phase comparator 213, a flaw data generating device 214. Each phase shifter 206 of the added signal generating modules $RA_1$ to $RA_9$ is connected to one input side of the adder 211 and each band pass filter 210 of the received signal interfaces $RB_1$ to $RB_9$ is connected to the other input side of the adder 211. The output side of the adder 211 is connected to a flaw data terminal $RT_5$ through the waveform shaping circuit 212, the phase comparator 213, the flaw detecting signal generating device 214. The compare signal terminals $T_1$ to $T_9$ of the exciting signal generating circuit 201 are connected to a comparing input side of the phase comparator 213 through each comparing terminal $RT_4$ of each module side of the received signal processing module $RQ_1$ to $RQ_9$.

In the flaw detector for metal material having the above construction illustrated in FIG. 2, when exciting signal $F_0$ is supplied to the exciting coil EC of the remote field eddy sensor PRB, received signal $f_1$ to $f_9$ is generated in the receiving coil $RC_1$ to $RC_9$. The received signal $f_1$ to $f_9$, whose in-phase noise is removed by the differential amplifier 207 and whose high frequency component is removed by the low pass filter 208, are supplied to another input side of the adder 211. On the other hand, the exciting signal $f_0$ applied to the adding terminal $RT_1$ of the added signal processing modules $RCC_1$ to $RCC_9$ is attenuated to a level set in an amplitude setting device 205a of the attenuator 205 of the added signal generating modules $RA_1$ to $RA_9$. Then if, in the phase shifter 206, a phase angle is set to a predetermined phase angle, for example 15 degrees, in a phase angle setting device 206a, the added signals phase angle is delayed by 15 degrees, is transmitted to one input side of the received signal processing modules $RQ_1$ to $RQ_9$. In the adder 211, since the received signal $f_0$ to $f_9$ generated in a pipeline to be tested is added with the added signal, phase noise is removed by the adder 211, and the received signals $f_0$ to $f_9$ having constant level are applied from the output side of the adder 211 to the phase comparator 213. Thus, in the phase comparator, stable phase detection can be performed. Since stable phase detection can be performed, normal flaw data is supplied to the flaw data terminal $RT_5$ and errors in diagnosing shape, depth and location of the flaw part caused by accumulation of noise generated abnormal flaw data can be prevented.

Figure 3:
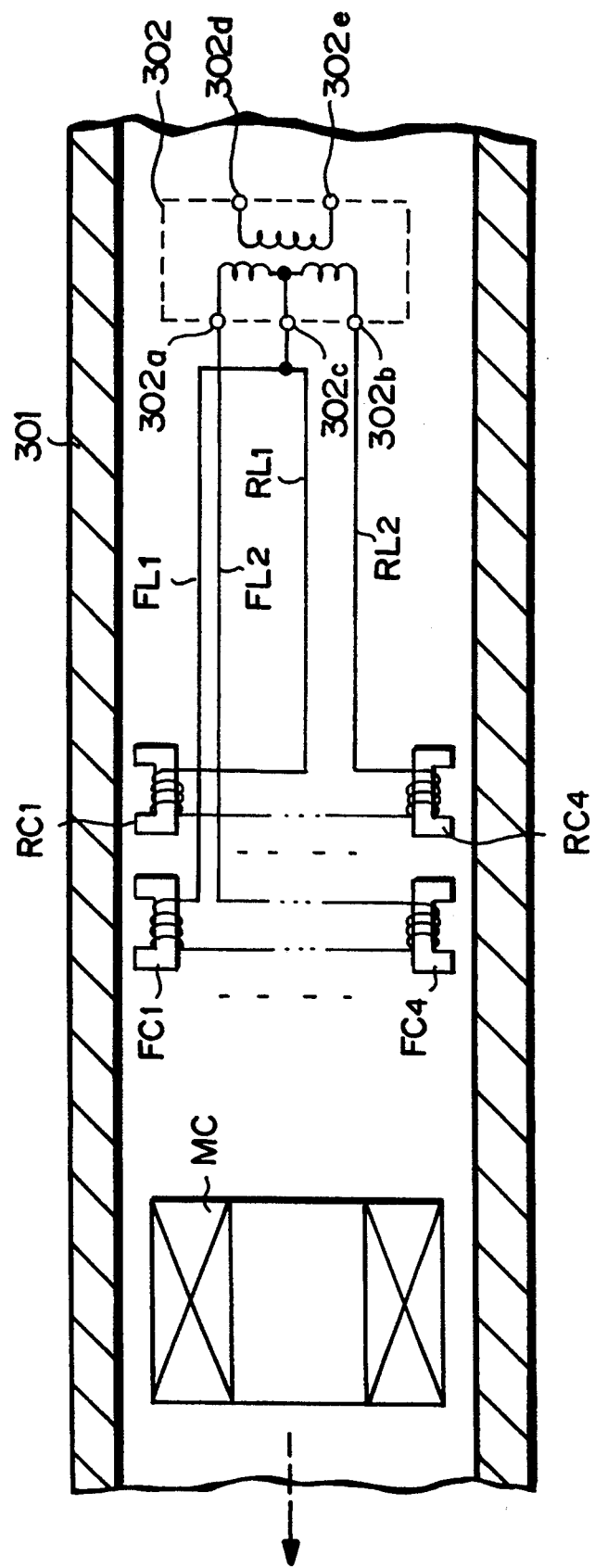
FIG. 3 is a block diagram of a remote field eddy current sensor according to the present invention.
Figure 4:
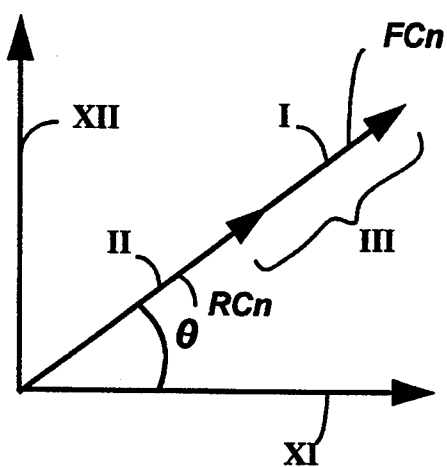
FIG. 4 is a signal vector diagram of a normal pipeline associated with FIG. 1.

FIG. 3 illustrates another embodiment of a remote field eddy current sensor according to the present invention.

In the FIG. 3, MC is an exciting coil. Forward receiving coils FCn (n is 1 to 6) are provided a predetermined distance from the exciting coil MC (about two times further than pipeline diameter). The forward received coils $FC_1$ to $FC_6$ are spaced from each other by 60 degrees with reference to a pipeline to be tested 301. That is, the forward receiving coil $FC_1$ is provided in a direction of twelve o'clock, $FC_2$ is provided in a direction of two o'clock ... $FC_9$ is provide in a direction of 4 o'clock. Each of the forward receiving coils $FC_1$ to $FC_6$ is connected serially and cables $FL_1$ and $FL_2$ drawn therefrom are connected to terminals 302c and 302a of a differential coils 302. Further, rear receiving coils $RC_n$ (n is 1 to 6) are provided at the rear of the forward receiving coils $FC_1$ to $FC_6$. The number of turns of the rear coils $RC_1$ to $RC_6$ is fewer than that of the forward receiving coils $FC_1$ to $FC_6$. The rear coils $RC_1$ to $RC_6$ are provided in the same orientation as that of the forward receiving coils $FC_1$ to $FC_6$, respectively. That is, the rear receiving coils $RC_1$ are provided at 12 o'clock.

The rear receiving coils $FC_1$ to $RC_6$ are connected in series and are connected to terminals 302c and 302b of the differential coil 302 through cables $RL_1$ and $RL_2$.

One end of the rear receiving coils RCn and one end of the forward receiving coils FCn are connected to each other and another end of the rear and forward receiving coils are drawn, respectively to construct a differential wire bound between the forward receiving coils FCn and the rear receiving coils FCn. In this wire bound construction, the differential coil can be eliminated.

When the remote field eddy current sensor having the above construction is provided to a normal part of the pipeline, a signal vector I (in this description, I, II ... is referred to as vector) by the forward receiving coils FCn has same phase R as that of a signal vector II by the rear receiving coils RCn, since both coils are provided in adjacent position. Vector III is a differential vector by the differential wire bound. Vector III equals I subtracted by II and has the phase R, since their directions are same. When the signal vector III is detected by reference signal vector XI, phase data R of the normal, nonflawed part of the pipe can be obtained. Traditionally, since vector III is a small value in the equation of I−II=III, the phase detection for vector III becomes unstable and stable data cannot be obtained. In the remote field eddy current sensor according to the present invention, however, the signal level of the forward receiving coils FCn is greater than that of the rear receiving coils RCn whose distance from the exciting coil MC is further than that of the forward receiving coils FCn, and the number of turns of the forward receiving coils FCn is greater than that of the rear receiving coil. Thus, additional offset signal level is added to vector I so that enough signal level of the differential vector III can be obtained to perform stable phase detection.

Figure 5:
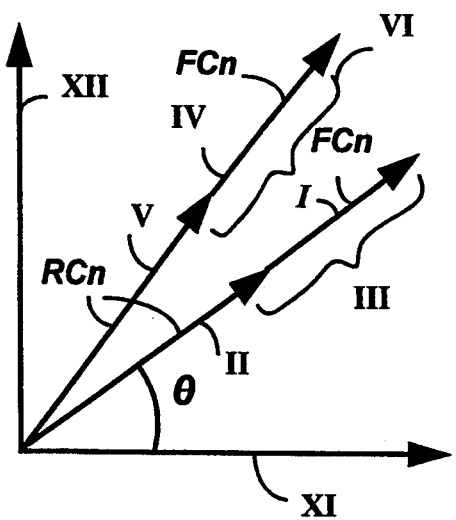
FIG. 5 is a signal vector changing diagram of gradually progressing flaw associated with FIG. 1.

FIG. 5 illustrates change of the signal vectors as to a large gradually flaw progressing part FW. In the drawing, signal vector I is signal vector of a normal part by the forward receiving coils FCn. II is signal vector of the normal part by the rear receiving coils FCn and III is signal vector of the normal part by the differential wire bound. Since the gradually flaw progressing part FW ranges over a wide area, both of the forward receiving coils and the rear receiving coils are included in the flaw part and both signal vectors change simultaneously. Further, IV is a signal vector of a gradually flaw progressing part by the forward receiving coils FCn, V is signal vector of the gradually flaw progressing part by the rear receiving coils RCn and VI is signal vector of the gradually flaw progressing part by the differential wire bound. VI is included in the gradually flaw progressing part FW and the gradually flaw part FW can be detected by using the phase difference between III and IV.

In FIG. 6, I is signal vector of a normal part by the forward receiving coils FCn and II is signal vector of the normal part by the rear receiving coils RCn and III is signal vector of the normal part by the differential wire bound. Since the local flaw part ranges in a small area of the pipe. Only the forward receiving coils FCn are included in the flaw areas. Considering the case wherein only the signal vector I changes, IV is signal vector of the local flaw part by the forward receiving coils FCn and V is signal vector of the local flaw part by the differential wire bound. The local flaw part FS can be detected by the differential phase between V and III.

FIG. 7 illustrates a receiving level by a distance between the exciting coil MC and the forward and the rear receiving coils FCn and RCn. In FIG. 7, a horizontal axis indicates the differential distance (MC−FCn or RCn) and a vertical axis indicates the received signal level. When using the forward receiving coils FCn having a greater number of turns than that of the rear receiving coils RCn to obtain the required receiving signal level, the number of turns must be increased in order to compensate the decreased signal level of the receiving signal level. Therefore, it is apparent from the characteristics view that when a forward receiving coils FCn having greater number of turns than that of the rear receiving coils RCn are provided forward, signal level is increased by positioning the FCn coils close to the exciting coil MC and by increasing the number of turns of FCn coil to get a stable signal level.

In the above embodiment, number of the forward receiving coils and the rear receiving coil are not limited to six. The receiving coils can be connected in parallel and any number of the coils can be selected. The method for connecting the forward and rear receiving coils FCn and RCn is not limited to the above embodiment, and any wiring which performs the differential operation will obtain the same advantages.

The remote field eddy current sensor according to the present invention has such advantages that more stable phase data with reference to both of the gradually flaw progressing part and the local flaw part can be obtained in comparison with the prior system.

What is claimed is:

1. A remote field eddy current flaw detector for detecting flaws in a metal pipe, comprising:
   a reference signal generator for generating a reference signal;
   an exciting coil for receiving an exciting signal having the same phase as that of said reference signal and generating remote field eddy current signals in the metal pipe to be tested;
   a receiving coil, spaced axially from said exciting coil by a predetermined axial distance, for receiving said remote field eddy current signals that have passed through said pipe to generate a received signal;
   an attenuator for attenuating said exciting signal at a predetermined level;
   a phase shifter for delaying the attenuated signal to a predetermined phase angle;
   a signal adder for adding the attenuated and delayed signal to said received signal; and
   a flaw data generator for phase-comparing the added signal generated by said signal adder with said reference signal to generate a flaw signal representative of flaws in the metal pipe.

2. A remote field eddy current flaw detector for metal pipe according to claim 1, further comprising: plural receiving coils wherein each receiving coil is associated with a corresponding attenuator, phase shifter, signal adder and flaw data generator.

* * * * *